Figure 1A:
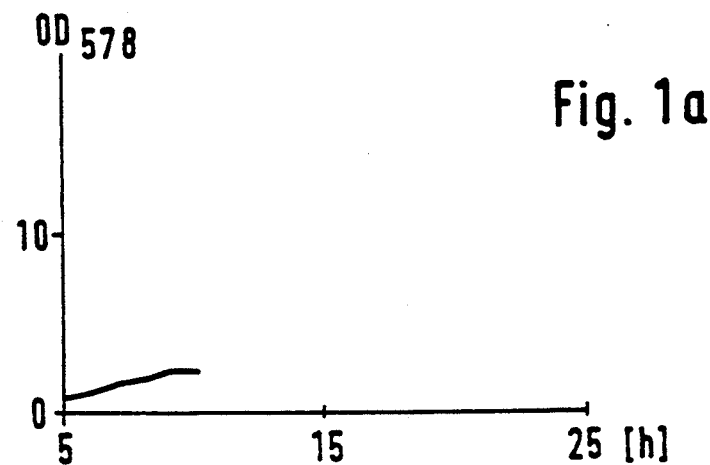

United States Patent [19]

Heinrich et al.

[11] Patent Number: 5,196,317
[45] Date of Patent: * Mar. 23, 1993

[54] OVEREXPRESSION OF PROTEINS IN RECOMBINANT HOST CELLS

[75] Inventors: Martin Heinrich, Darmstadt; Wolfgang Ebeling, Bickenbach; Wolfgang Brümmer, Alsbach-Hähnlein, all of Fed. Rep. of Germany

[73] Assignee: Merck Patent Gesellschaft mit beschränkter Haftung, Darmstadt, Fed. Rep. of Germany

[*] Notice: The portion of the term of this patent subsequent to Jun. 30, 2009 has been disclaimed.

[21] Appl. No.: 608,443

[22] Filed: Nov. 2, 1990

[30] Foreign Application Priority Data

Nov. 2, 1989 [DE] Fed. Rep. of Germany ....... 3936408

[51] Int. Cl.$^5$ ............... C12N 15/00; C12N 15/53; C12N 15/67; C12N 15/70
[52] U.S. Cl. ............... 435/69.1; 435/190; 435/252.3; 435/252.33; 435/248; 935/39; 935/43; 935/61; 935/72; 935/73
[58] Field of Search .............. 435/69.1–69.9, 435/172.1–172.3, 252.3–252.35, 320.1; 536/27

[56] References Cited

U.S. PATENT DOCUMENTS 4,894,334  1/1990  Ben-Bassat et al. ............. 435/69.1

FOREIGN PATENT DOCUMENTS 0285949  3/1988  European Pat. Off.
0290768  11/1988  European Pat. Off.

OTHER PUBLICATIONS

Rinas, U., et al., 1989, Applied Microbiology and Biotechnology 31:163–167.
Okita, B., et al. 1989, Biotechnology and Bioengineering 34:854–862.
Kopetzki, E., et al., 1989, Molecular and General Genetics 216:149–155.
Sugimoto, S., et al., 1987, Journal of Biotechnology 5:237–253.
Osburne, M. S., et al., 1985, Journal of Bacteriology 163(3):1101–1108.
Remaut, E., et al., 1983, Nucleic Acids Research, 11(14):4677–4688.

Primary Examiner—Robert A. Wax
Assistant Examiner—William Moore
Attorney, Agent, or Firm—Millen, White, Zelano and Branigan

[57] ABSTRACT

The invention relates to a process for achieving high, thermally-induced expression rates, which last for a relatively long period of time, of proteins in recombinant cells, preferably in E. coli cells, by optimizing cell density, induction temperature and supplemented amino-acid-containing substrates.

14 Claims, 8 Drawing Sheets

OVEREXPRESSION OF PROTEINS IN RECOMBINANT HOST CELLS

BACKGROUND OF THE INVENTION

The invention relates to a process for achieving high, thermally induced expression rates, which last for a relatively long period of time, of proteins, e.g., enzymes, in recombinant host cells, in particular *E. coli*, by means of mutually suited cultivation parameters such as cell density, induction temperature and added amino-acid-containing substrates.

It is the aim of every genetic engineering process to obtain, in particular, maximum possible yields of recombinant product. To date, a two-phase process has proved to be successful for this purpose. First optimum growth of the cells is aimed at for this purpose, in order to achieve a large biomass and amount of plasmid. At the same time, care has to be taken that, while growth is good, the amount of waste product, e.g., acetate, accumulated is not too high. In this first phase more than a negligible production of the recombinant protein is undesired, since the cell growth is, in some cases, greatly reduced by excessive substrate consumption and/or by the overproduction of the recombinant protein which, in some cases, also has a toxic effect. For this reason it is important that an expression system which can be regulated is available. In such a system, the promoter is repressed during the growth phase of the cells so that there is little or no production of recombinant protein. In a second phase at a high cell density or large biomass, the promoter is derepressed and the expression is induced thereby. Numerous expression systems which can be regulated and in which the induction of protein expression is effected by a temperature shift or by chemical induction are known for microorganisms. One of the best known and most efficient promoters for *E. coli* is the lambda $P_L$ promoter which is, for example, described in EP-A-0,041,767. The CI857 repressor which blocks the promoter is thermally inactivated by a temperature shift to about 42° C., and the transcription of the structural gene is thus made possible (phase 2). Many enzymes and other proteins have to date been expressed by employing such a two-phase standard procedure in *E. coli*, thus, for example, EcoRI restriction endonuclease (Bottermann et al., Biotechnol, Bioeng. 27 (1985), p. 1320), α-amylase (Reinikainen et al., Biotechnol. Lett. 10 (3) (1988), p. 149), mutarotase (EP-A-0,307,730) or glucose dehydrogenase (EP-A-0,290,768). Growth and expression do not necessarily have to be sequential in one reactor in this procedure, but may also take place in two separate reactors in series.

However, the mentioned procedure which has hitherto been used in practice and is also used, in modified form and using other promoter systems which can be regulated for other species of bacteria, such as Bacillus, often has disadvantages which, in specific cases, can make the process impracticable. Thus, a decrease, which is severe in some cases, in the growth rate of the recombinant host cells is observed in most cases when the number of plasmid replications increases and, connected thereto, the overexpression of protein is increased (for example, Bently and Kompala; Biotechn. Bioeng. 33 (1989) p. 49).

Furthermore, it is known that a derepression of the promoter, for example by a temperature shift, can lead to a severe restriction of growth and to high losses of plasmid (for example, Siegel and Ryu, Biotechn. Bioeng. 27 (1985), p. 28). Furthermore, noteworthy is the frequent observation (for example, Peretti and Bailey, Biotechn. Bioeng. 32 (1988), p. 418) that, immediately after promoter induction, there is initially a very high recombinant protein biosynthesis rate, although this is usually only short-lasting and then decreases more or less rapidly. All these effects cause the net synthesis rate to be limited by the decrease in growth rate after promoter induction has taken place. Thus, not only is the yield of recombinant protein, in absolute terms, often insufficient but also new recombinant host cells have to be continually cultivated since the old cells become unproductive after a relatively short time and, in most cases, can no longer be regenerated. This is an economic disadvantage.

Thus, the object was to eliminate the above-mentioned disadvantages in the production of proteins and enzymes with the aid of host cells containing recombinant promoters which can be regulated by optimizing the cultivation parameters and to make possible high recombinant protein biosynthesis rates for a long period of time.

SUMMARY OF THE INVENTION

It has now been found that the yields and/or activities of proteins, e.g., enzymes, prepared by recombinant techniques can be increased 5 to 10 fold, and the biosynthesis can be maintained at a high level for a longer period of time than hitherto, if the promoter activation which initiates the protein expression is carried out (1) at a biomass which is just moderate, not waiting until it is at a maximum as practiced hitherto, in a relatively early growth phase of the recombinant host cells, (2) at an induction temperature of below 40° C. and (3) in the presence of added amino-acid-containing substrates Activities of 200 to 500, preferably 250 to 350 U/ml of culture broth and a specific activity of 100 to 300, preferably of 150 to 250 U/mg of protein can be achieved, for example, for the enzyme glucose dehydrogenase prepared by genetic engineering.

The invention thus relates to a process for the preparation of proteins by cultivating recombinant host cells in a nutrient solution and by temperature-induced expression and subsequent isolation of the proteins, characterized in that the expression of the proteins is carried out.

a) at a biomass of the recombinant host cells present at the beginning of the induction which is equivalent to 5 to 40% of the maximum achievable biomass,
  b) at an induction temperature of <40° C. and
  c) in the presence of added amino acids and/or yeast extracts.

The invention particularly relates to a corresponding process, which is characterized in that the recombinant host cells are *E. coli* cells, the expression of the proteins is controlled by the lambda $P_L$ promoter, and the added mixture of amino acids contains at least phenylalanine, tyrosine and tryptophan.

The invention also particularly relates to a expressed protein is glucose dehydrogenase.

Various other objects, features and attendant advantages of the present invention will be more fully appreciated as the same becomes better understood when considered in conjunction with the accompanying drawings, and wherein:

FIG. 1 shows the expression of Gluc-DH according to the experimental conditions of Example 1 (comparison value, induction temperature 42° C., $OD_{578}=2.5$, no additives);

FIG. 2: As 1, but at large biomass ($OD_{578}$ 10);

FIG. 3: As 2, induction temperature: 39° C.;

FIG. 4: Expression of Gluc-DH at moderate biomass ($OD_{578}=2.5$), induction temperature: 39° C., addition of phenylalanine, tyrosine and tryptophan.;

FIG. 5: As 4, but addition of yeast extract without further amino acids at $OD_{578}=5.0$;

FIG. 6: As 5, but with additional supplementation with phenylalanine, tyrosine and tryptophan;

FIG. 7: As 4, but complete spectrum of amino acids at $OD_{578}=3.5$; and

Figure 8A:
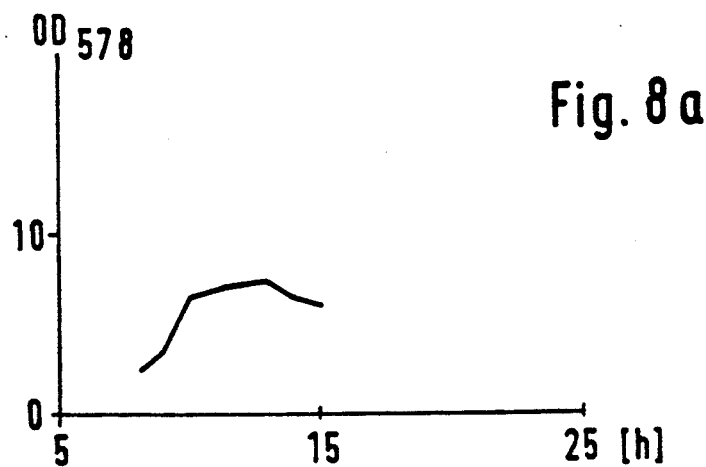
Figure 8B:
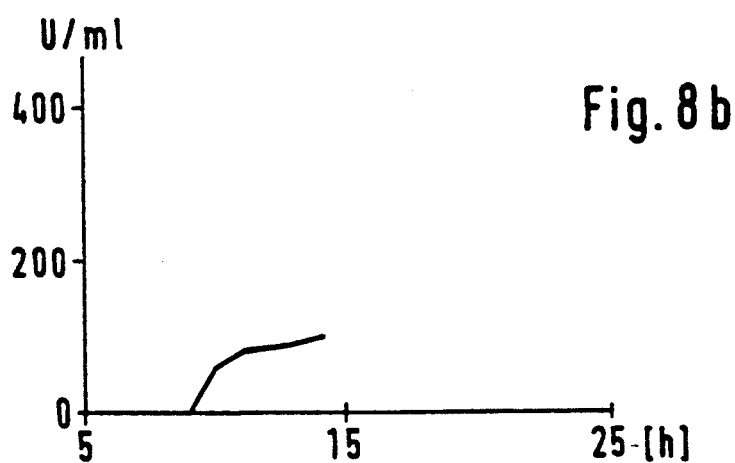
Figure 8C:
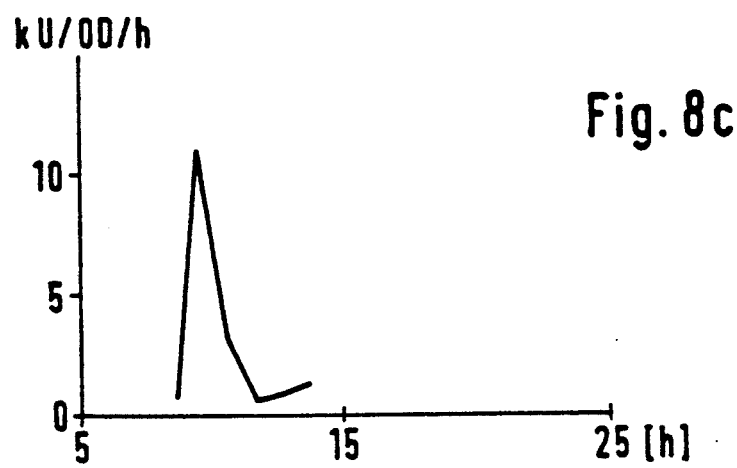

FIG. 8: As 6, but induction temperature of 42° C. at $OD_{578}=2.5$.

The figures show diagrams which depict the optical density in OD units at 578 nm (a), the enzyme activity in units/ml (b) and the biomass-specific expression rate in kilounits/OD/h (c) as a function of the time in hours after the inoculation (abscissa) with varying process parameters. In all cases, the same recombinant *E. coli* host strain (see text and Example 1) which is capable of the expression of glucose dehydrogenase (Gluc-DH) by thermal induction is cultivated and worked up.

Host cells suitable for carrying out the process according to the invention are, in principle, all recombinant transformed host cells of microbial origin, in which the structural gene to be expressed is controlled by at least one promoter which can be regulated and is thermally inducible. *E. coli* and Bacillus species are particularly suitable microorganisms. Recombinant *E. coli* host cells are particularly preferred. Suitable promoters which can be regulated are all promoters which are efficient in the particular microorganism, in particular the *E. coli* lambda $P_L$ promoter, the corresponding lac, trp or tet promoter or else hybrid promoters if they can be thermally regulated. The lambda $P_L$ promoter disclosed in EP-A-001,767 which can be induced by an increase in temperature to 42° C. is particularly preferred.

The type and origin of the structural gene to be expressed does not play a crucial part in carrying out the process according to the invention. Thus, every structural gene capable of being expressed in the particular microorganism is, in principle, suitable.

The advantageous characteristics of the process according to the invention must always be seen in direct comparison with the otherwise identical process of the prior art, that is to say in comparison with the expression of the same structural gene with an identical plasmid construction in the same microorganism. Suitable structural genes are, for example, glucose dehydrogenase genes, the mutarotase gene and the genes for sorbitol dehydrogenase, chloramphenicol acetyltransferase and dihydrofolate reductase.

The process according to the invention is preferably carried out as follows.

Any desired *E. coli* strain (for example, *E. coli* K 12 or *E. coli* N 100) which has been transformed with an appropriate expression vector is, for example, used as recombinant microorganism. The structural gene is preferably controlled by the thermally-inducible lambda $P_L$ promoter.

In a preferred embodiment, the *E. coli* strain N 100/pRK 248/pJH 115 (DSM 4047) is used. The strain is disclosed in EP-A-0,290,768 and has been transformed with the vector pJH 115. Plasmid pJH 115 contains the glucose dehydrogenase gene from *Bacillus megaterium*.

The appropriate *E. coli* strain is cultivated by standard methods in known growth media customary for this purpose. The growth of the cells is monitored in a known manner by measuring the optical density or the turbidity of the culture medium by spectrophotometry, preferably at 578 nm. According to the invention the cells are left to grow only up to a moderate biomass (early to middle growth phase) before the temperature shift is carried out. It is equivalent to 5 to 40%, preferably 10 to 20%, of the maximum biomass of the particular recombinant host strain achievable under the given cultivation conditions. As a rule this is equivalent to a biomass corresponding to a turbidity of 2.0 to 5.5 OD, preferably of 2.5 to 4.5 OD, measured at 578 nm. Normally the maximum biomasses which can be achieved correspond to a turbidity of 8 to 10 OD (578 nm). However, in exceptional cases even markedly lower OD values may also be measured at maximum achievable cell densities. The particular measuring apparatus used (cuvette size, spectrophotometer, etc.) also plays a certain part. However, it is always essential to the invention that the activation of the promoter by an increase in temperature and the protein expression started thereby is begun at a biomass which, as mentioned above, is markedly below the maximum achievable cell density.

The temperature in the growth phase (no thermally-inducible protein expression) is maintained between 25° and 35° C., preferably between 28° and 32° C. At the desired cell density, the temperature is increased to 37° to 40° C., preferably to 38° to 39° C., and the expression is thereby started. This temperature is markedly lower than required for an optimum induction of the lambda $P_L$ promoter (42° C.). Surprisingly, this proves not to diminish the enzyme activities or the protein yields but to make possible a marked increase if all process parameters according to the invention are adhered to.

Immediately before or after, preferably before, the increase in temperature takes place, amino-acid-containing substrates are added to the culture medium in the process according to the invention. Mixtures of single amino acids, yeast extracts or else mixtures of amino acids and yeasts extract can be used as substrates in this connection.

Suitable examples are thus aspartic acid, glutamic acid, serine, glutamine, glycine, threonine, arginine, alanine, tyrosine, tryptophan, valine, phenylalanine, lysine, leucine, isoleucine and proline, but other naturally occurring amino acids can also be used. Those mixtures which contain at least phenylalanine, tyrosine and tryptophan are preferred in this connection.

Suitable yeast extracts can be obtained by suspending any of the well known, conventional, and commercial yeast cultures in water or buffer as described below.

The concentration of the added amino acids varies according to the invention between 0.05 g/l and 1.0 g/l per amino acid, preferably between 0.1 g/l and 0.5 g/l. The alternative yeast extract is added in a concentration of from 1 g/l to 10 g/l, preferably from 4 to 6 g/l. Particularly high enzyme activities/protein yields can be achieved if a complete spectrum of amino acids is added. Alternatively, mixtures of yeast extract and amino acids, in particular the three aromatic amino acids phenylalanine, tyrosine and tryptophan, can also be used.

Each individual feature of the process according to the invention has a more or less pronounced effect with respect to an increased expression rate. This can be seen from the examples below and the figures. However, the really significant increases in expression to 5- to 10-times of the comparison value (process parameters according to the prior art) for a relatively long period of time can be observed only when a combination of the three parameters according to the invention—moderate biomass, reduced induction temperature and supplementation with amino-acid-containing substrates—is used. In the process according to the invention a considerable expression can be maintained for a period of time of 4 to 8 hours, while in the comparison example the expression almost comes to a halt after just 2 to 3 hours.

After expression is substantially complete, the cells are worked up by standard methods, such as described, for example, in EP-A-0,290,768 or in EP-A-0,307,730, the expressed protein is isolated and purified in a customary manner and the expression rate or the enzyme activity is determined in a known manner. The methods used in this connection depend on the type of protein expressed in each case.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 39 36 408.9, filed Nov. 2, 1989, are hereby incorporated by reference.

EXAMPLES

EXAMPLE 1

*E. coli* N 100/pRK 248/pJH 115 (DSM 4047) is cultivated in a nutrient solution essentially containing

Figure 1B:
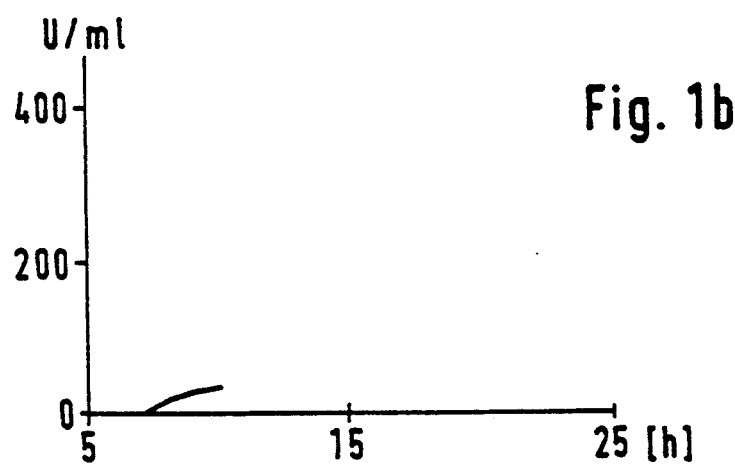
Figure 1C:
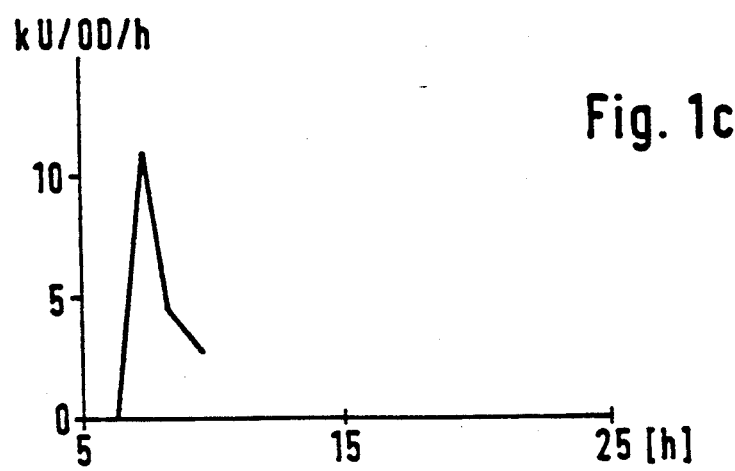

| | % (w/v) |
|---|---|
| Na$_2$HPO$_4$ × 2H$_2$O | 0.19 |
| KH$_2$PO$_4$ | 0.075 |
| NH$_4$Cl | 0.4 |
| MgSO$_4$ × 7H$_2$O | 0.1 |
| Citric acid | 0.2 |
| Glucose | 0.1 |
| CaCl$_2$-X-2H$_2$O | 0.01 | in a 100 liter fermenter at 32° C. During the growth phase, cell growth is monitored by measuring the optical density at 578 nm at regular intervals. At an optical density of 2.5 (reached 7 to 10 hours after inoculation) the temperature is increased to 42° C. and the cells are allowed to grow for a further 5 h. The glucose dehydrogenase activity is measured at regular intervals by the activity assay which is specified, for example, in EP-A-0,290,768. Subsequently, the cells are spun down at 20° C. (5000 rpm), taken up in a sodium phosphate buffer (0.1 mol/l, pH 6.5) and homogenized in a high pressure homogenizer at 1000 bar while cooling. 35% PEG 1500 (polyethylene glycol) is stirred into the homogenate in the course of 20 to 25 minutes. After the PEG has dissolved, 67% (w/v homogenate) of the following phosphate buffer are metered in at pH 5.2 (±0.1) while stirring (data in % w/w: NaH$_2$PO$_4$×2H$_2$O 26.2%, K$_2$HPO$_4$ 1.3%, pH 4.7). 6% (w/v homogenate) of NaCl are then added and the mixture is stirred for another 2 h. The phases are separated by centrifugation. The upper phase containing glucose hydrogenase (Gluc-DH) can undergo filtration or diafiltration, if necessary. Glucose dehydrogenase having an activity of 40 U/ml is obtained (FIG. 1a–c).

EXAMPLE 2

Figure 2A:
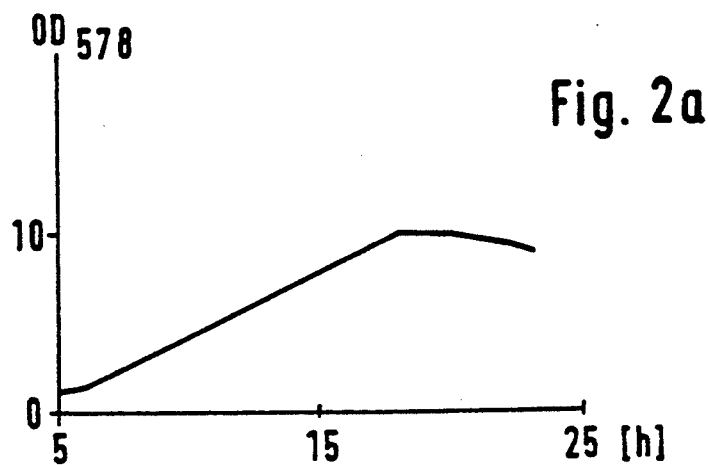
Figure 2B:
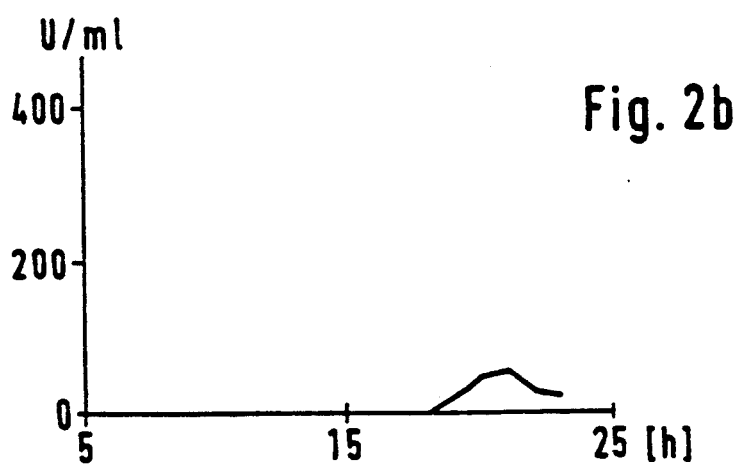
Figure 2C:
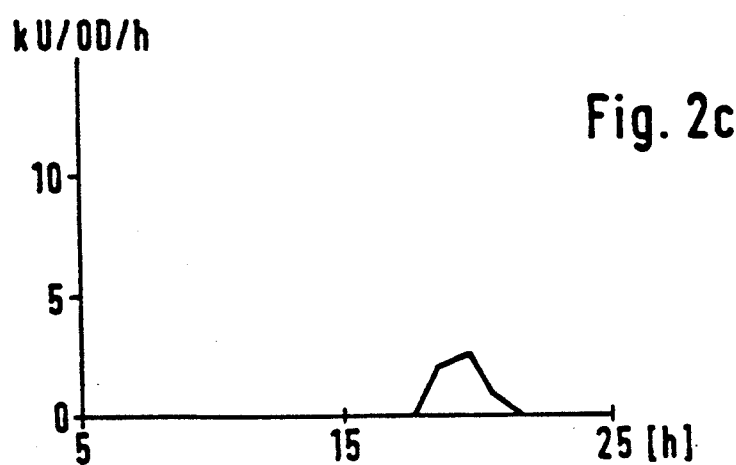

The growing of the recombinant host cells and the expression and isolation of Gluc-DH are carried out in analogy to Example 1. However, the cells are allowed to grow until an optical density of 10 is reached (maximum biomass) before the expression is started. The result is 50 U/ml, that is a slightly increased enzyme activity or biomass specific expression rate (FIG. 2a–c).

EXAMPLE 3

Figure 3A:
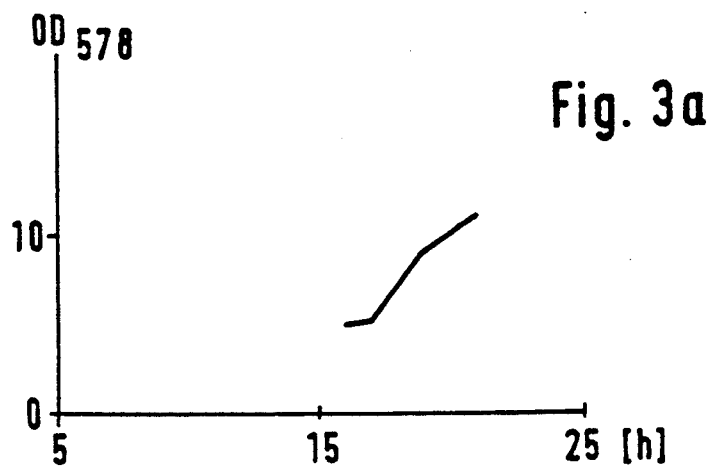
Figure 3B:
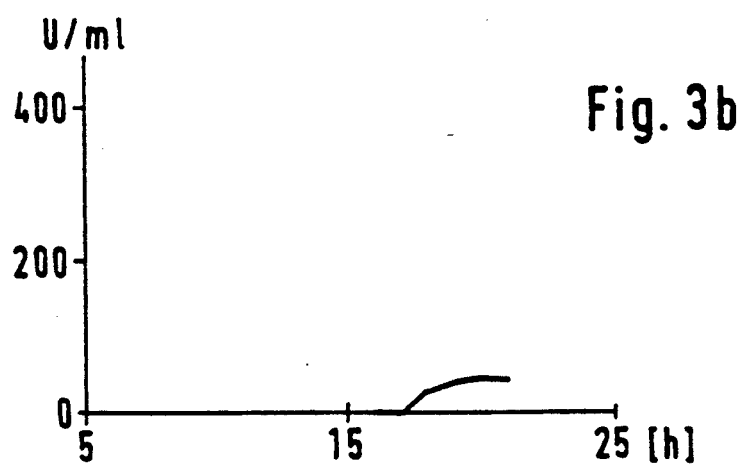
Figure 3C:
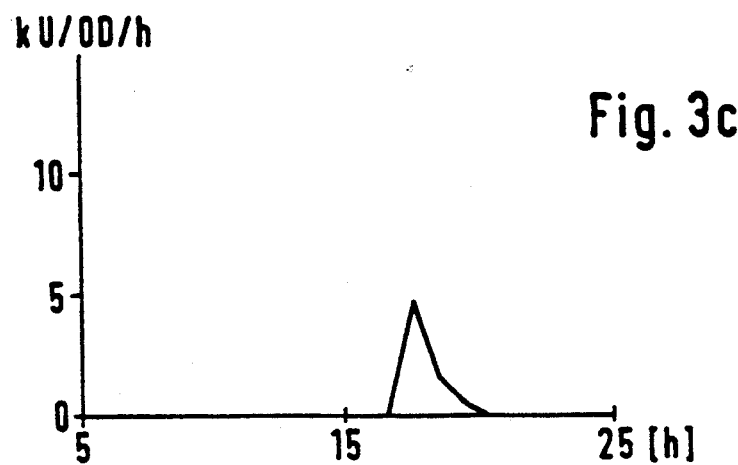

The growing of the recombinant host cells and the expression and isolation of Gluc-DH are carried out in analogy to Example 2, but the temperature is increased merely to 39° C. Activities and yields are as in Example 2 (FIG. 3a–c).

EXAMPLE 4

Figure 4A:
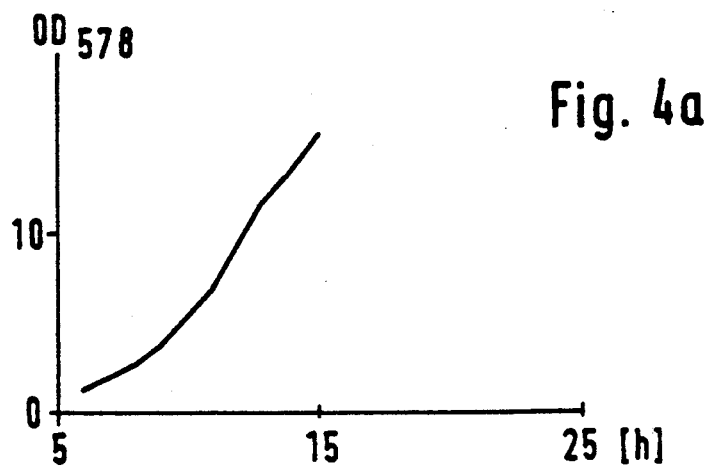
Figure 4B:
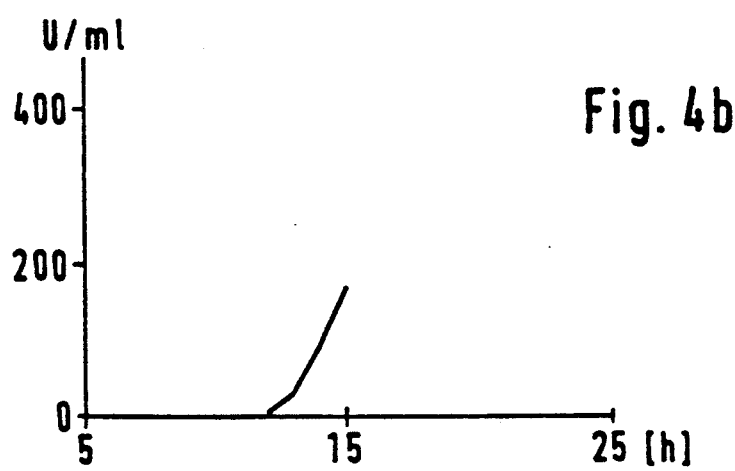
Figure 4C:
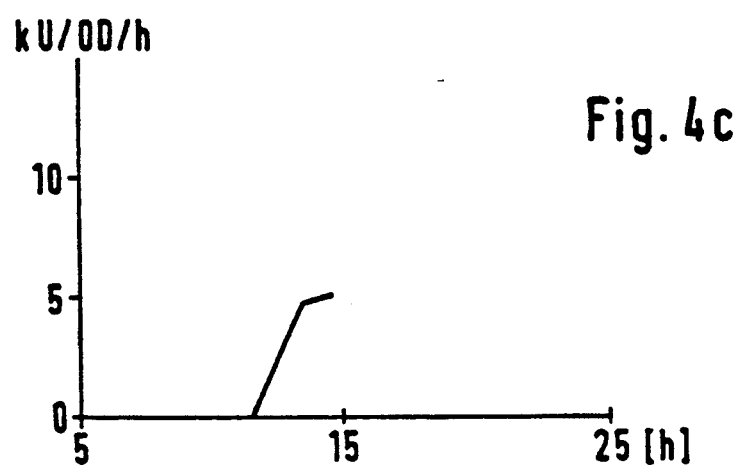

The growing of the recombinant host cells and the expression and isolation of Gluc-DH are carried out in analogy to Example 1. At an optical density OD of 2.5, 0.3 g/l each of tryptophan, tyrosine and phenylalanine are added. The temperature of the culture broth is increased to 39° C. immediately afterwards. An enzyme activity of 170 U/ml is achieved (FIG. 4a–c).

EXAMPLE 5

Figure 5A:
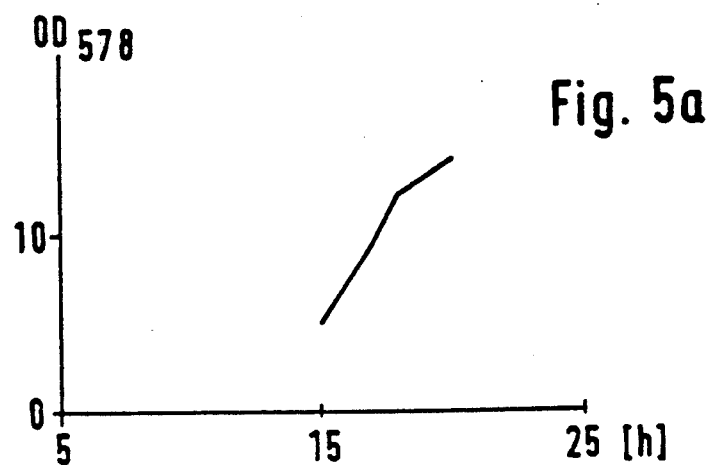
Figure 5B:
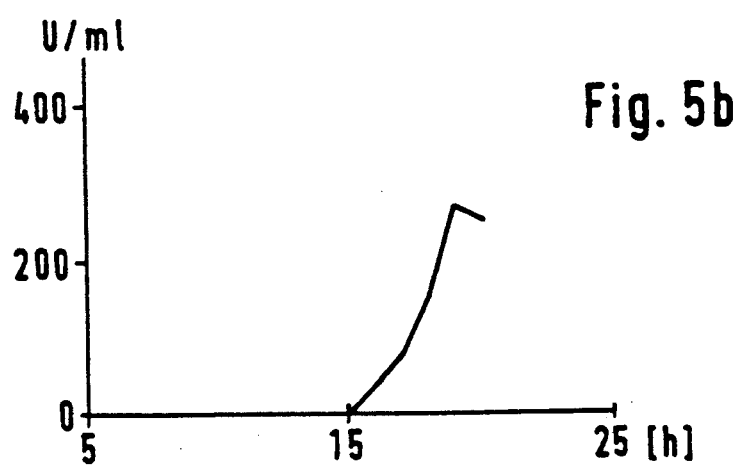
Figure 5C:
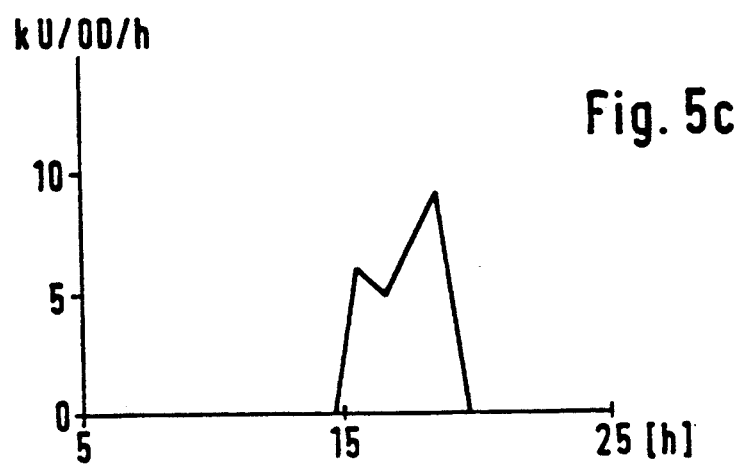

The growing of the recombinant host cells and the expression and isolation of Gluc-DH are carried out in analogy to Example 4. In place of the amino acid mixture, a yeast extract (5 gl) is added at OD=5.0. An enzyme activity of 270 U/ml and a maximum biomass-specific expression rate of 9 kU/OD/h are achieved (FIG. 5a–c).

EXAMPLE 6

Figure 6A:
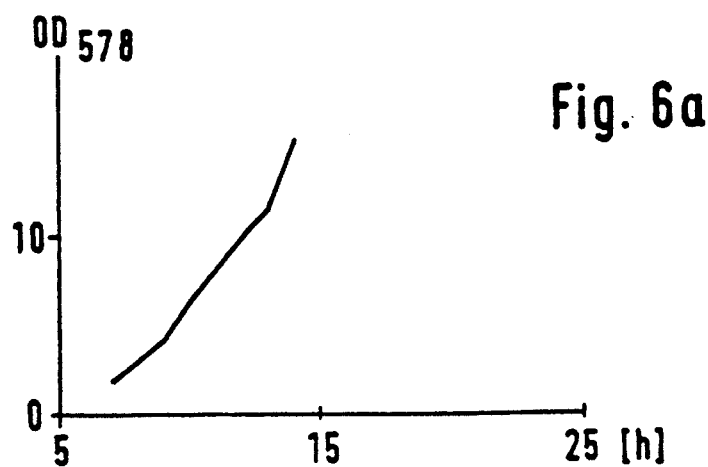
Figure 6B:
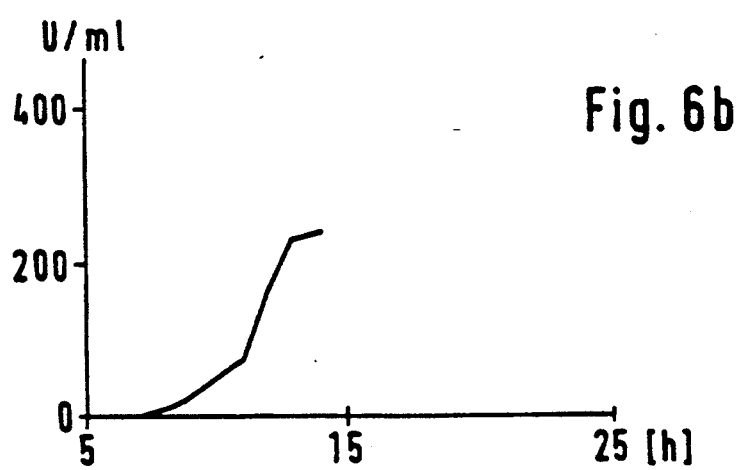
Figure 6C:
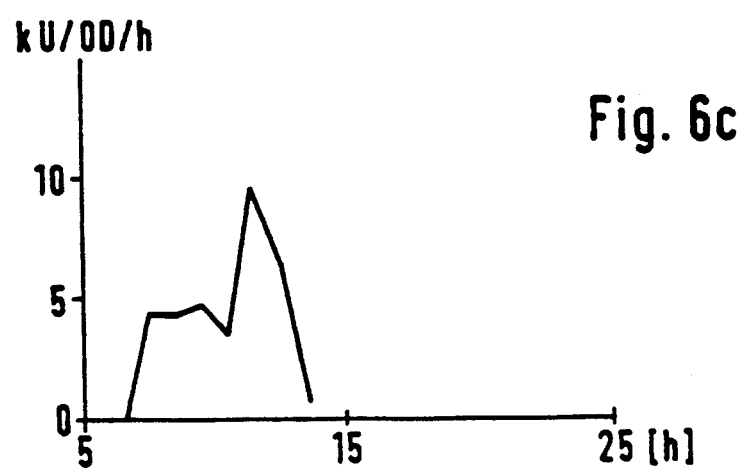

The growing of the recombinant host cells and the expression and isolation of Gluc-DH are carried out in analogy to Example 4. When an optical density OD of 2.0 is reached, a yeast extract (5 g/l) and additionally the amino acids phenylalanine, tyrosine and tryptophan in a concentration of 0.2 g/l each are added before the temperature is increased to 39° C. The biosynthesis of Gluc-DH lasts for a period of time of 7 h. An activity of 240 U/ml can be achieved (FIG. 6a–c).

EXAMPLE 7

Figure 7A:
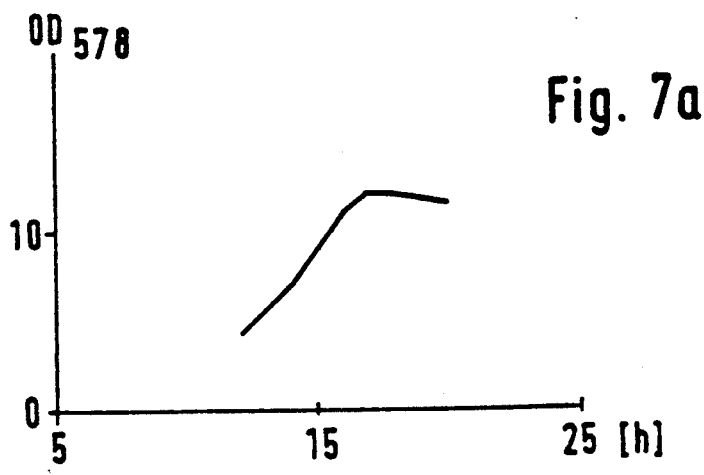
Figure 7B:
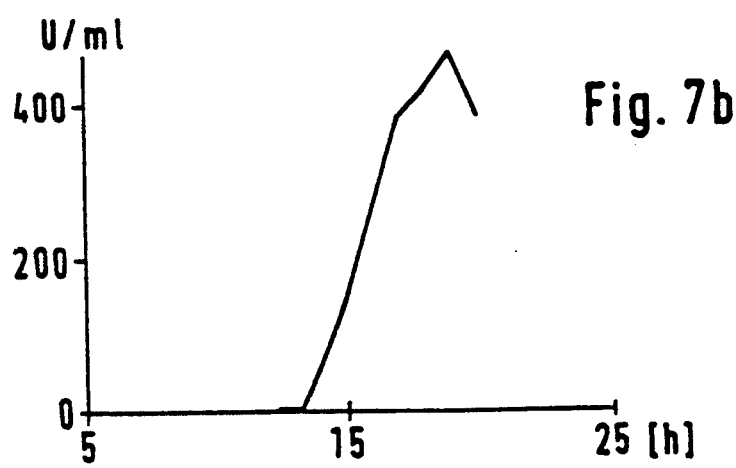
Figure 7C:
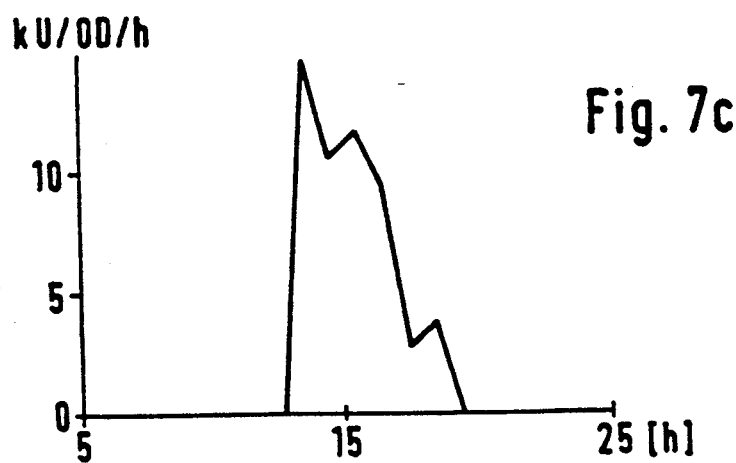

The growing of the recombinant cells and the expression and isolation of Gluc-DH are carried out in analogy to Example 4. When an optical density OD of 3.5 is reached, a mixture of all naturally occurring amino acids in a concentration of 0.1 g/l each is added before the temperature is increased to 39° C. An activity of 460 U/ml and a maximum biomass-specific expression rate of about 14 kU/OD/h are achieved. The biosynthetic activity persists for about 7 h in this case too (FIG. 7a–c).

EXAMPLE 8

The growing of the recombinant cells and the expression and isolation of Gluc-DH are carried out in analogy to Example 6. However, after the addition of the appropriate substrates at OD=2.5, the temperature is increased to 42° C. As in Example 1, a short-lasting high, but then greatly decreasing biosynthesis rate which leads to an enzyme activity of 95 U/ml is observed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the preparation of a protein by cultivating recombinant prokaryotic host cells in a nutrient solution and by expression of the protein with a thermally-inducible promoter system and subsequent isolation of the protein, the improvement comprising carrying out the expression of the protein
   (a) at a biomass of the recombinant host cells present at the beginning of induction of expression which is equivalent to 5 to 40% of the maximum achievable biomass,
   (b) at a suboptimal expression temperature and
   (c) in the presence of one or more added amino acids and/or a yeast extract,
   whereby the thus-produced protein is biologically active.

2. A process of claim 1, wherein the recombinant host cells are *E. coli*.

3. A process of claim 2, wherein the expression of the protein is controlled by a lambda $P_L$ promoter and a CI857 repressor.

4. A process of claim 3, wherein the expression of the protein is carried out at a temperature of 37° to 40° C.

5. A process of claim 1, wherein the added amino acids comprise phenylalanine, tyrosine and tryptophan.

6. A process of claim 1, wherein the expressed protein is glucose dehydrogenase.

7. A process of claim 1, wherein the recombinant host cells are Bacillus.

8. A process of claim 2, wherein the expressed protein is glucose dehydrogenase.

9. A process of claim 8, wherein a yield of specific activity of 150 to 250 U/mg of protein is achieved.

10. A process of claim 4, wherein the expression of the protein is carried out at a temperature of 38° to 39° C.

11. A process of claim 1, wherein the expressed protein is derived from a prokaryote.

12. A process of claim 10, wherein the expressed protein is derived from a prokaryote.

13. A process of claim 1, wherein the suboptimal expression temperature is at least 2° C. lower than the optimal expression temperature for said thermally-inducible promoter system.

14. A process of claim 12, wherein the expressed protein is glucose dehydrogenase.

* * * * *